United States Patent [19]
Jang et al.

[11] Patent Number: 5,895,397
[45] Date of Patent: Apr. 20, 1999

[54] INTRAVASCULAR CATHETER HAVING COMBINED IMAGING ABRASION HEAD

[75] Inventors: Yue-Teh Jang, Fremont; William Martin Belef, San Jose, both of Calif.

[73] Assignee: Cardiovascular Imaging Systems, Inc., San Jose, Calif.

[*] Notice: This patent is subject to a terminal disclaimer.

[21] Appl. No.: 08/706,017

[22] Filed: Aug. 30, 1996

Related U.S. Application Data

[63] Continuation of application No. 08/468,254, Jun. 6, 1995, Pat. No. 5,569,276, which is a continuation of application No. 08/293,831, Aug. 22, 1994, Pat. No. 5,507,292, which is a continuation of application No. 07/842,813, Feb. 27, 1992, Pat. No. 5,402,790, which is a continuation of application No. 07/526,413, May 21, 1990, Pat. No. 5,100,424.

[51] Int. Cl.$^6$ ............................................. A61B 17/22
[52] U.S. Cl. ................. 606/159; 128/898; 604/22
[58] Field of Search ............ 606/159; 128/660.03, 128/662.06, 898; 604/96–103, 22

[56] References Cited

U.S. PATENT DOCUMENTS

| | | |
|---|---|---|
| Re. 33,569 | 4/1991 | Gifford, III. |
| 3,889,657 | 6/1975 | Baumgarten. |
| 4,243,049 | 1/1981 | Goodale et al. ............... 606/159 |
| 4,445,509 | 5/1984 | Auth ............................... 606/159 |
| 4,465,072 | 8/1984 | Taheri. |
| 4,616,648 | 10/1986 | Simpson. |
| 4,631,052 | 12/1986 | Kensey. |
| 4,646,736 | 3/1987 | Auth ............................... 606/159 |
| 4,669,469 | 6/1987 | Gifford, III. |
| 4,685,458 | 8/1987 | Leckrone ....................... 606/159 |
| 4,747,821 | 5/1988 | Kensey et al.. |
| 4,756,309 | 7/1988 | Sachse et al. ................. 128/305 |
| 4,771,774 | 9/1988 | Simpson. |
| 4,781,186 | 11/1988 | Simpson. |
| 4,794,928 | 1/1989 | Kletschka. |
| 4,794,931 | 1/1989 | Yock. |
| 4,795,438 | 1/1989 | Kensey et al.. |
| 4,842,578 | 6/1989 | Johnson et al.. |
| 4,850,957 | 7/1989 | Summers ...................... 604/22 |
| 4,857,045 | 8/1989 | Rydell. |
| 4,857,046 | 8/1989 | Stevens et al.. |
| 4,867,157 | 9/1989 | McGurk-Burleson et al. .... 606/180 X |
| 4,883,458 | 11/1989 | Shiber ........................... 604/22 |
| 4,886,061 | 12/1989 | Fischell et al. ............... 604/22 |
| 4,894,051 | 1/1990 | Shiber ........................... 604/22 |
| 4,926,858 | 5/1990 | Gifford, III. |

(List continued on next page.)

FOREIGN PATENT DOCUMENTS

| | | |
|---|---|---|
| 0347098 | 7/1989 | European Pat. Off.. |
| 041915 4A1 | 9/1990 | European Pat. Off.. |
| 3601453 A1 | 2/1985 | Germany. |
| 37322 36C1 | 9/1987 | Germany. |
| 3626684A1 | 8/1996 | Germany. |
| WO89/00023 | 1/1989 | WIPO. |

OTHER PUBLICATIONS

European Search Report for EP 96 10 4718, Dec. 1996.

*Primary Examiner*—Michael Powell Buiz
*Assistant Examiner*—Daphna Shai
*Attorney, Agent, or Firm*—Lyon & Lyon LLP

[57] ABSTRACT

Front-end and side-on intravascular catheters are described that comprise an abrasive head contained substantially within a housing. Aspiration means and flushing means are connected to the region of grinding to remove dislodged debris. A preferred embodiment has the abrasive surface of a rotatable head comprised of diamond powder. Another preferred embodiment has an ultrasonic transducer affixed to the head to permit transluminal imaging of the site of occlusion.

56 Claims, 4 Drawing Sheets

U.S. PATENT DOCUMENTS

| | | | |
|---|---|---|---|
| 4,950,278 | 8/1990 | Sachse et al. | 606/170 |
| 4,951,677 | 8/1990 | Crowley et al. . | |
| 4,979,939 | 12/1990 | Shiber | 606/159 |
| 4,979,951 | 12/1990 | Simpson . | |
| 4,984,563 | 1/1991 | Renaud | 128/6 |
| 5,024,651 | 6/1991 | Shiber | 604/22 |
| 5,041,089 | 8/1991 | Mueller . | |
| 5,047,040 | 9/1991 | Simpson . | |
| 5,053,044 | 10/1991 | Mueller . | |
| 5,071,425 | 12/1991 | Gifford, III . | |
| 5,084,010 | 1/1992 | Plaia . | |
| 5,092,873 | 3/1992 | Simpson . | |
| 5,100,424 | 3/1992 | Jang et al. | 608/159 |
| 5,100,425 | 3/1992 | Fischell et al. | 606/159 |
| 5,135,531 | 8/1992 | Shiber | 606/159 |
| 5,402,790 | 4/1995 | Jang et al. | 606/159 |
| 5,507,292 | 4/1996 | Jang et al. | 606/159 |
| 5,569,276 | 10/1996 | Jang et al. | 606/159 |

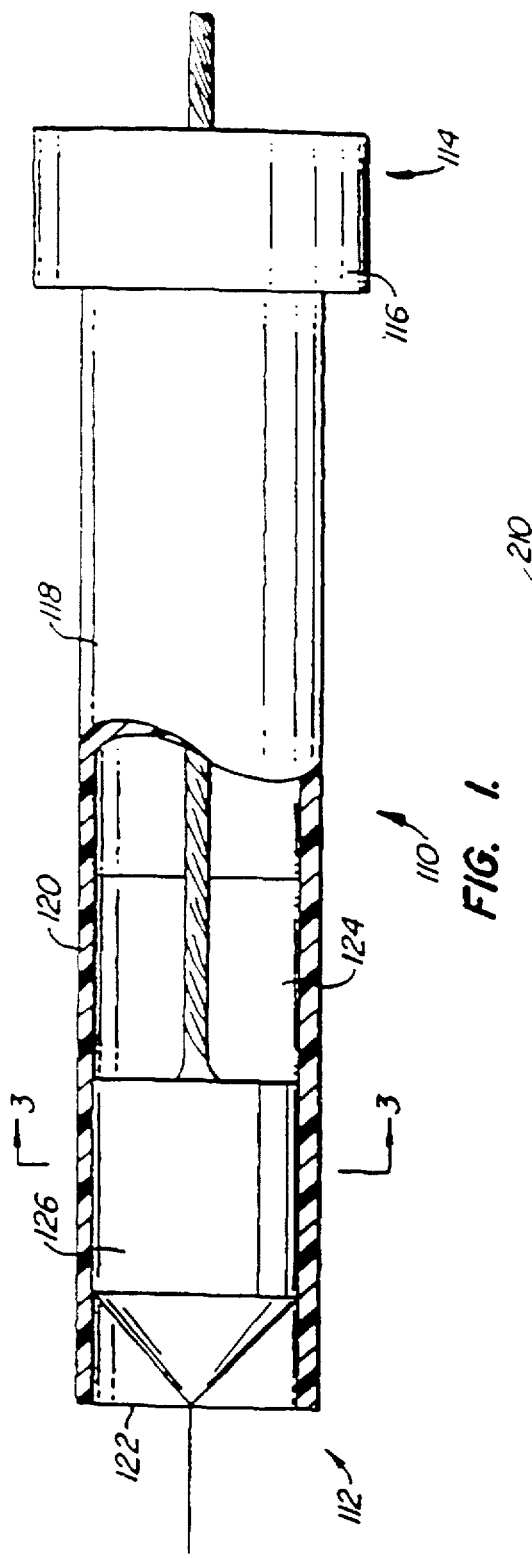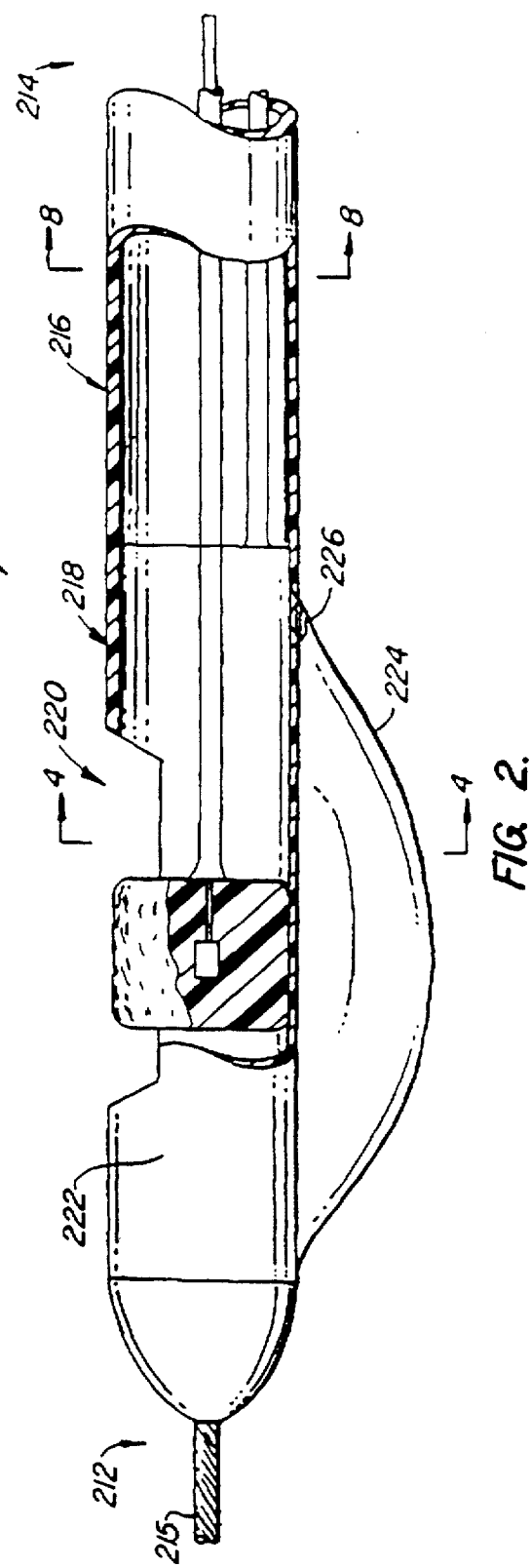

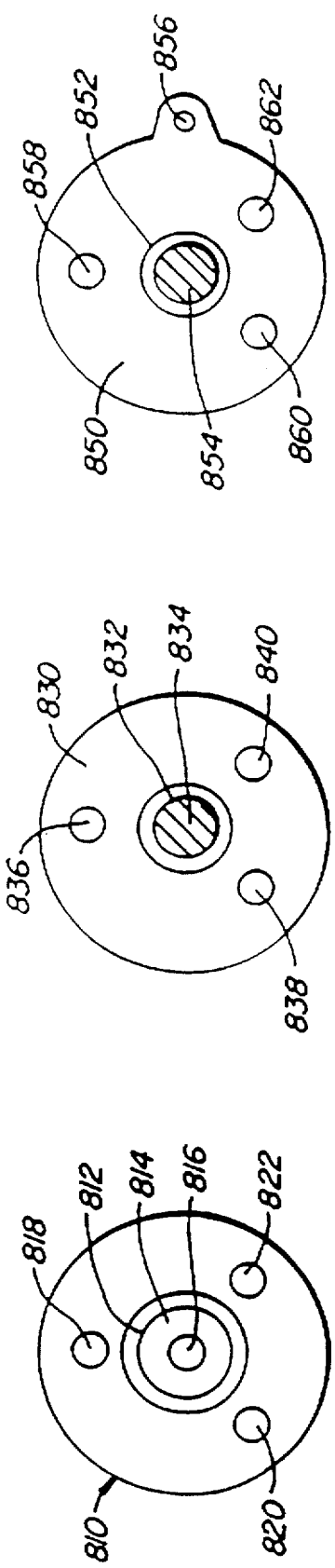
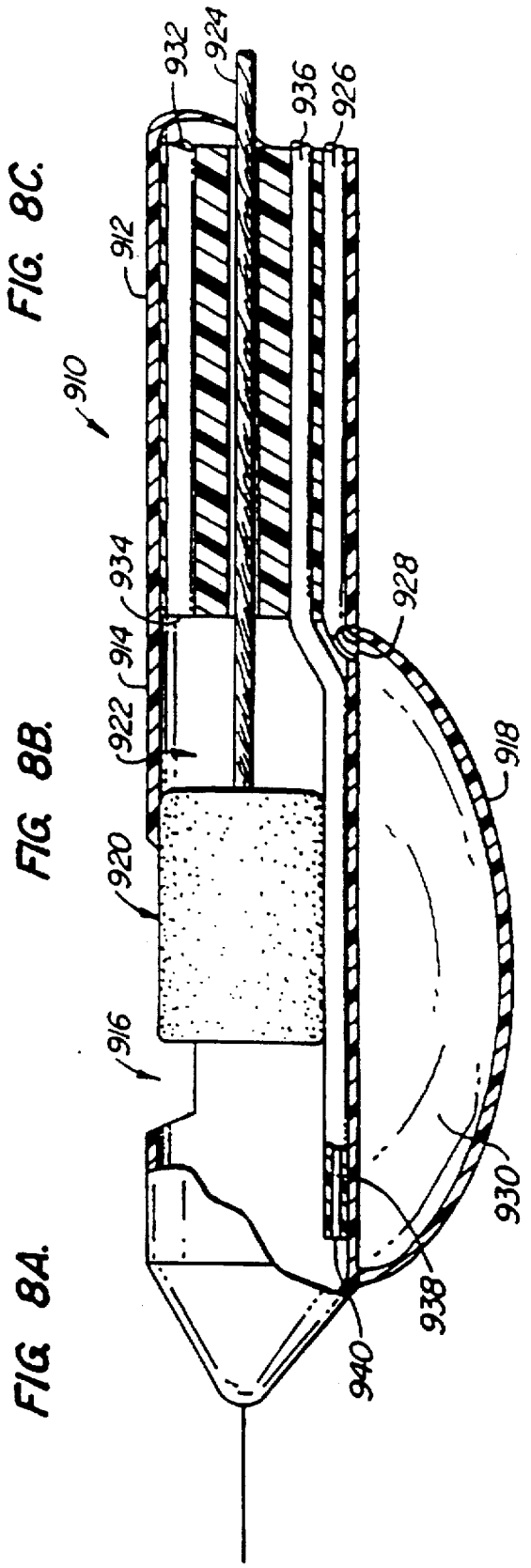
FIG. 8A.   FIG. 8B.   FIG. 8C.   FIG. 9.

INTRAVASCULAR CATHETER HAVING COMBINED IMAGING ABRASION HEAD

This is a continuation of application Ser. No. 08/468,254, filed on Jun. 6, 1995, now U.S. Pat. No. 5,569,276, which is a continuation of U.S. application Ser. No. 08/293,831, filed Aug. 22, 1994, now U.S. Pat. No. 5,507,292, which is a continuation of U.S. application Ser. No. 842,813, filed Feb. 27, 1992, now U.S. Pat. No. 5,402,790, which is a continuation of U.S. application Ser. No. 526,413, filed May 21, 1990, now U.S. Pat. No. 5,100,424. All of the above-identified applications and patents are expressly incorporated herein by reference.

BACKGROUND OF THE INVENTION

1. Field of the Invention

The present invention relates generally to vascular catheters. More particularly, the present invention relates to atherectomy catheters capable of performing abrasion atherectomy, optionally in combination with transluminal imaging.

The blood vessels of human beings commonly become constricted due to the deposition of fatty substances, e.g., lipoproteins, on the interior of the vessel walls. This condition, known as arteriosclerosis, or atherosclerosis, occurs naturally as a part of the aging process. The condition may also be promoted by such factors as heredity, diet, hypertension, and cigarette smoke. The vascular deposits result in a restriction of blood flow and in serious cases can place a person's health at risk. In acute cases the restriction can result in stroke, hemorrhage, etc. Initially, the fatty deposits are relatively soft; however, over time they become fibrotic and hardened.

Numerous approaches for reducing and removing intravascular deposits have been proposed. The deposits, called atheromas or atherosclerotic plaques, can be reshaped by dilatation of an inflatable balloon located at the distal end of an angioplasty catheter.

Alternatively, atheromas can be removed from the vessel wall by cutting, grinding, or thermal ablation, e.g., via laser angioplasty. Of particular interest to the present invention are atherectomy catheters that remove atheromas from the vessel wall by cutting or grinding.

In a typical atherectomy operation, a catheter of appropriate diameter is introduced into a patient's vascular system and positioned adjacent the occluding atheroma. The distal end of the catheter is provided with a blade which is brought into contact with the atheroma. The catheter may either be a terminal (front-end) cutting type or a side-cutting type. Side-cutting atherectomy catheters frequently employ an inflatable balloon located opposite the blade to firmly engage the blade with the atheroma.

However, the above devices have certain deficiencies. In particular, the blades of the cutting element may slice into too much of the occluding material at one time, thereby causing release of large emboli and/or rupture of the vessel wall. Moreover, if the emboli are not promptly captured and removed from the patient's body, they may pass through the vascular system until they become wedged in narrow points of the vascular channels. If an embolus becomes lodged in a critical region of the vascular system, e.g., a coronary artery, the patient's health can be placed seriously at risk.

The release of large emboli into the vascular system is particularly problematic when front-end catheters are employed. Front-end devices generally employ a cutting element which extends beyond the distal end of a casing for the cutting element. See, for example, U.S. Pat. No. 4,857,046. Thus, relatively large particles can be dislodged from the atheroma. Additionally, the dislodged particles generally remain outside the casing of the cutting element, free from entrapment by the catheter. If such particles are not promptly collected they will circulate freely through the vascular system as emboli.

Side-cutting catheters generally reduce the likelihood that emboli will be released into the vascular system since the housing in which the blades are at least partially contained can passively collect dislodged particles. The collected particles can be removed from the patient's vascular system upon retraction of the catheter. See, U.S. Pat. No. 4,794,931. However, many particles can be expected to escape entrapment within the catheter in such a device.

Several methods have been proposed for remedying the shortcomings identified above one approach is to modify the impacting head in order to channel dislodged particles into the catheter. See, for example, U.S. Pat. No. 4,857,046 which describes an auger-like mechanism for collecting particles. Another approach is to provide an aspiration means for actively removing particles from the vascular system. See, for example, U.S. Pat. No. 4,857,045. Still other approaches involve modifying the impacting head to reduce the size of the dislodged particles in an effort to minimize the risk to the patient presented by large emboli. See, for example, FIG. 4 of U.S. Pat. No. 4,857,045. None of the approaches proposed for reducing the size of particles and for capturing and withdrawing the particles provides a satisfactory solution for these problems.

For these reasons it is desirable to provide catheters that grind atheromas into very small debris particles. Also, it is desirable to remove those particles via catheters provided with flushing and aspiration means for removing the particles. Such devices are expected to significantly reduce the potential for release of large emboli. Additionally, it is desired to provide a means for transluminally imaging the site of atherectomy in order to determine the location and extent of removal of the undesired tissue.

2. Description of the Background Art

U.S. Pat. Nos. 4,857,046, 4,857,045, 4,842,578, 4,747,821, 4,631,052, and 4,795,438 all describe front-end intravascular catheter devices. None of the references describe devices that grind away atherosclerotic plaques via an impacting head that is substantially contained within a housing. Nor do the devices utilize an inflatable balloon means to aid engagement of the impacting head with the undesired tissue. U.S. Pat. No. 4,794,931 describes a catheter having a rotary impacting head which removes sclerotic material through a side window provided in a housing. An opposing balloon is provided to assist placement of the head adjacent the undesired material. U.S. Pat. Nos. 4,794,928; 4,465,072; and 3,889,657 relate to catheter designs intended to scrape blood vessels and other body lumens.

Various techniques for transluminal imaging of the diseased region of a vessel wall have been proposed, including endoscopic and ultrasonic imaging techniques. See, for example, U.S. Pat. No. 4,794,931 which describes an ultrasonic transducer attached to the hub of a rotary head. See, also, commonly-assigned copending application Ser. No. 366,906 which describes a laser catheter having transluminal imaging capability, and copending application Ser. No. 500,641 which describes a combined balloon angioplasty/imaging catheter.

SUMMARY OF THE INVENTION

According to the present invention, intravascular catheters for removing stenotic material from a patient's vascular system comprise an elongate catheter body having proximal and distal ends. A housing is secured to the distal end of the catheter body and the housing is provided with an aperture in one of its side walls. A head for abrading stenotic material is provided substantially within the housing so that any material that penetrates the aperture can be abraded and captured within the housing. Dislodged material is withdrawn from within the housing by means for withdrawing the material provided internal the catheter.

A preferred embodiment of the invention has an aspirating means connected to the interior of the housing via an axial lumen provided in the catheter body. Abraded stenotic material is thereby aspirated from the patient's body. Additionally, grooves (or channels) may be provided axially or helically along the exterior of the abrasive head or along the interior wall of the housing. Such grooves assist in transport of abraded material from distal the head to points proximal the head. A flushing means located external the patient's body may also be employed to augment removal of material from within the catheter housing.

Another preferred embodiment has a transluminal imaging means affixed to the head for abrading the stenotic material. Preferably, the transluminal imaging means is afforded by an ultrasonic transducer.

A further preferred embodiment of the invention employs at least one inflatable balloon attached to the housing. Inflation of the balloon(s) assists in contacting the stenotic material with the abrasive head when the housing aperture is provided in a side wall of the housing.

A still further preferred embodiment of the invention employs a rotatable member substantially within the housing for abrading stenotic material that penetrates the housing aperture. Placement of the rotary member within the housing helps ensure that dislodged particles collect inside the housing. The rotatable member is able to abrade stenotic material, e.g., by provision of an abrasive surface. Exemplary surfaces of the rotatable member are comprised of diamond powder and fused silica, tungsten carbide, aluminum oxide, boron carbide, and the like. The rotatable member can have an axial lumen through which a guidewire may be passed. Imaging of the site of occlusion may be provided by an ultrasonic transducer affixed to the rotatable member.

The present invention affords novel methods for removing stenotic material from a patient's vascular system. The methods comprise the steps of introducing the distal end of a catheter into the vascular system and positioning the aperture of the housing located at the distal end of the catheter body proximate the stenotic material. An abrasive member located substantially within the housing is engaged against the stenotic material through translational and/or rotational motion of the abrasive member. Abraded material is withdrawn from the patient's body via means for withdrawing the material, e.g., by aspiration of the region within the housing.

The present invention thereby affords superior grinding devices and methods for removing stenotic material from a patient's vascular system.

BRIEF DESCRIPTION OF THE DRAWINGS

FIG. 1 is a detail view of the distal region of a front-end catheter constructed in accordance with the principles of the present invention.

FIG. 2 is a detail view of the distal region of a side-on catheter constructed in accordance with the principles of the present invention.

FIGS. 8A–C show cross-sectional views of alternative catheter bodies constructed according to the principles of the present invention (FIG. 8A is taken along line 8—8 of FIG. 2).

FIG. 9 is a detail view of a side-on catheter having an alternative design for provision of means for withdrawing abraded material.

DETAILED DESCRIPTION OF THE PREFERRED EMBODIMENTS

Figure 3:
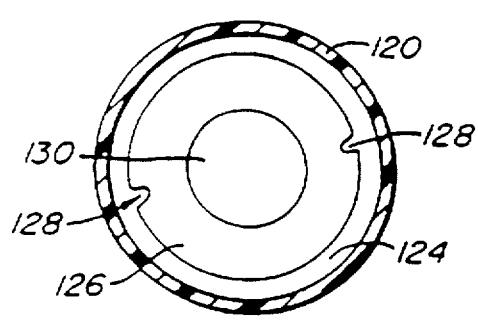
FIG. 3 is a cross-sectional view taken along line 3—3 of FIG. 1.

According to the present invention, intravascular catheters will include an elongated catheter body having distal and proximal ends. The catheter body will include an abrasive head for abrading stenotic material at the distal end of the catheter body. Preferably, the abrasive head will be provided by an abrasive rotatable member contained substantially within the housing. The housing will be provided with an aperture to permit intrusion of the stenotic material into the housing cavity. At least part of the periphery of the aperture is expected to contact target stenotic material during operation of the abrasive head, thereby assisting in containment of particles released by the grinding process. Also, means for withdrawing abraded material from within the housing to a point external the patient is provided. Preferably, an aspirating means in communication with the interior of the housing via an axial lumen in the catheter body will be employed as the means for withdrawing abraded material.

In a preferred embodiment, the aperture of the housing located at the distal end of the catheter will be provided in a side wall of the housing. One or more inflatable balloons will be optionally provided opposite the aperture to permit anchoring the distal end of the catheter adjacent a target stenosis.

The stenotic material that can be abraded by the present devices includes all naturally occurring occlusions of vascular walls, e.g., atherosclerotic plaques, lipoprotein deposits, blood clots, hemorrhaged tissues, etc.

Catheters constructed according to the present invention also may include a transluminal imaging means affixed to the abrasive head. Such imaging means preferably will be provided by ultrasonic transducers. Suitable transducers are described in U.S. Pat. No. 4,794,931, which is incorporated herein by reference.

A. Catheter Bodies

The vascular catheters of the present invention will comprise a catheter body having distal and proximal ends. The catheter body will be flexible to permit its passage through the vascular system of a patient. Preferably the catheter body will be comprised of a flexible transparent thermoplastic that affords ready visual inspection for air bubbles inside the catheter body. The catheter body will preferably have a smooth tubular shape; however, the catheter body may have a ridged structure, particularly when it is desired to provide a lumen, e.g., a guidewire lumen, along the longitudinal axis of the catheter.

The catheter selected will have an outer diameter small enough to permit positioning adjacent the diseased region of the vessel wall. Typically, the outer diameter of catheters employed will be in the range from about 1 mm to 4 mm, usually being about 2.5 mm for peripheral arteries of adult humans and about 1.7 mm for coronary arteries. Catheters employed will typically have a length ranging from about 60 cm to 150 cm.

Referring now to FIG. 1, a front-end type vascular catheter constructed in accordance with the principles of the present invention includes an elongated catheter body 110 having distal 112 and proximal 114 ends. Catheter body 110 is connected at its proximal end 114 to a manifold (not shown) via manifold connector 116. Such manifold connector includes internally-threaded means for connecting catheter body 110 to the manifold and is well known to those skilled in the art. The distal end of the catheter may be adapted to accept a moveable guidewire, described more fully herein below.

Catheter body 110 is comprised of a flexible plastic tube 118 having an outer diameter suitable for insertion into the patient's target vessel. Plastic tube 118 is preferably comprised of a transparent thermoplastic to permit observation of air bubbles internal the tube. Tube 118 is flexible and includes at least one lumen extending from the distal end 112 to the proximal end 114 thereof. Additional lumens may be included as needed. The utility of such lumens is discussed in more detail below.

Catheter body 110 is provided at its distal end with housing 120. Housing 120 preferably is constructed from stainless steel and is attached to plastic tube 118 using conventional methods. See, for example, U.S. patent application Ser. Nos. 732,691 and 834,893 (now U.S. Pat. No. 4,794,931). In front-end type catheters an aperture 122 is provided in the distal tip of housing 120 to permit penetration of target stenotic material into housing cavity 124. Housing cavity 124 contains all void space within housing 120 and is defined at its distal end by the periphery of aperture 122 and at its proximal end by flexible tube 118. Abrasive head 126 is provided internal housing 120 and is capable of moving axially or rotationally within housing cavity 124. A cross-section of housing 120 along line 3—3 is presented in FIG. 3, which is discussed herein below.

FIG. 2 shows the distal region of a side-on catheter constructed in accordance with the principles of the present invention. Catheter body 210 has essentially the same dimensions and is constructed from essentially the same materials as front-end catheter bodies described above. Catheter body 210 has distal end 212 and proximal end 214 thereof. Proximal end 214 is connected to a conventional manifold connector (not shown). A conventional fixed guidewire 215, described more fully herein below, is secured to distal end 212. Flexible tube 216 is comprised of the same materials and has essentially the same configurations allowed for the corresponding tube for front-end catheters described above.

Flexible tube 216 is attached to housing 218 in conventional manner. Housing 218 is typically comprised of stainless steel and has a cylindrical shape. A portion of the sidewall of housing 218 is removed to present aperture 220, through which stenotic material may penetrate into housing cavity 222. The distal tip of housing 218 may optionally be provided with an orifice through which a guidewire can pass.

In a preferred embodiment, at least one inflatable balloon is provided external the housing so as to press the side of the housing having the aperture against the target stenotic material. For example, as shown in FIG. 2, inflatable balloon 224 is provided opposite aperture 220 and external to housing 218. Balloon 224 is securely attached to housing 218, e.g., via a suitable adhesive. The proximal extremity of balloon 224 is preferably bonded to flexible tube 216 via a heat-shrinkable material. Balloon 224 can be inflated by passing an inflation medium through an inflation orifice 226 provided proximate the proximal extremity of balloon 224. Other aspects of the inflatable balloon feature of side-on catheters are presented in U.S. Pat. No. 4,794,931 and are incorporated herein by reference.

Figure 4:
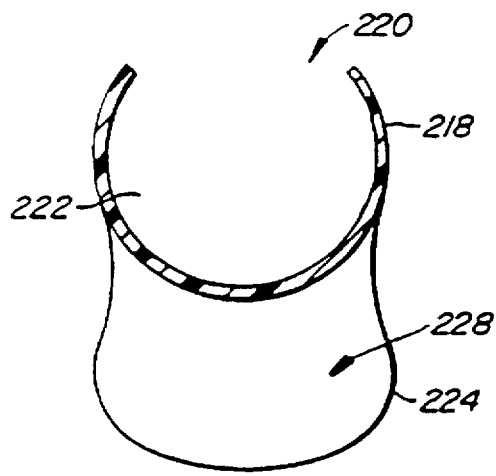
FIG. 4 is a cross-sectional view taken along line 4—4 of FIG. 2.

FIG. 4 presents a cross-sectional view of the side-on catheter of FIG. 2 taken along line 4—4 thereof. Thus, housing 218 defines housing cavity 222 and is provided with aperture 220 with balloon 224 provided opposite aperture 220.

B. Abrasive Heads

In the present invention, an abrasive head is provided at the distal end of the catheter body. The head is contained substantially within the housing located at the distal end of the catheter body. It is contemplated that a portion of the abrasive head may extend from within the housing to a point beyond the aperture provided in the housing; however, the entirety of the head will be contained within the housing sufficiently to ensure that dislodged stenotic material will be substantially contained within the housing.

The abrasive head may be comprised of a unitary abrasive material or may be a composite of a support material and an abrasive surface material affixed to the support. When an abrasive surface material is employed it may be adhesively bonded to the support by methods well known to those skilled in the art. Preferred abrasive materials comprising the surface of the abrasive head include fused silica, diamond powder, tungsten carbide, aluminum oxide, boron carbide, and other ceramic materials. Suitable abrasive materials are available commercially from Norton Company, Worcester, Mass.

When a composite abrasive surface and solid support is employed as the abrasive head of the present invention, a suitable support material must be identified. Generally, a suitable support will be any solid material that bonds effectively to the abrasive surface material with an adhesive. The support further must withstand the inertial and impact forces experienced during operation of the abrasive head.

A preferred support material is stainless steel. Also, the support preferably has an axial lumen to allow passage of a guidewire therethrough.

Typically, the abrasive head is attached to a drive means via a coupling provided at its proximal end. The drive means will extend axially through a lumen provided in the catheter body to a point external the patient's body. The drive means is connected to a drive motor which provides the power for driving the abrasive head. The drive means preferably includes an internal lumen which permits passage of a guidewire if desired.

Operation of the drive means is such that one revolution of the drive means causes one revolution of the abrasive head. During operation, the drive means will usually make 200–100,000 revolutions per minute. Also, translation of the drive means relative to the catheter body causes a translation of the abrasive head relative to the catheter body. Translation and rotation of the abrasive head via the drive means is afforded so as to permit the head to contact stenotic material

7 that penetrates the aperture of the housing. The construction and operation of drive means suitable for use in the present invention is further described in U.S. Pat. No. 4,794,931, which is incorporated by reference herein.

1. Front-end Catheters. When the catheter is of the front-end type, the abrasive head contained substantially within the housing will have an abrasive surface at the distal-most end of the head. Abrasive surfaces may also be provided elsewhere on the head. The proximal-most end of the head is in communication with a means for driving the head, e.g., a drive cable or a compressed fluid means.

FIG. 3 presents a cross-sectional view of the head and housing of the front-end type catheter shown in FIG. 1. Thus, an abrasive rotatable member 126 is provided internal housing 120 and is positioned so as to permit engaging rotatable member 124 with any stenotic material that penetrates the aperture 122 in the distal end 112 of housing 120. The rotatable member 126 need not be wholly contained within housing 120, i.e., the most distal region of the rotatable member may extend through aperture 122; however, rotatable member 126 must remain sufficiently within housing 120 such that the abrading surface of the rotatable member remains substantially within housing cavity 124 defined at its most distal end by aperture 122.

Grooves (or channels) are optionally provided axially along the exterior wall of the abrasive head to assist passage of dislodged material from the distalmost end of the housing to a point proximal the head. For example, FIG. 3 shows an abrasive rotatable member 126 provided within housing 120. The outer periphery of rotatable member 126 is provided with two grooves 128. An abrasive head having grooves may have only one groove or may have a plurality of grooves. Preferably, the grooves will be spaced equally about the periphery of the head; however, such equal spacing is not necessary. Abrasive rotatable member 126 is also provided with lumen 130 which permits passage of a guidewire therethrough and may also assist in the withdrawal of released particles from the distal region of the head.

Figure 5:
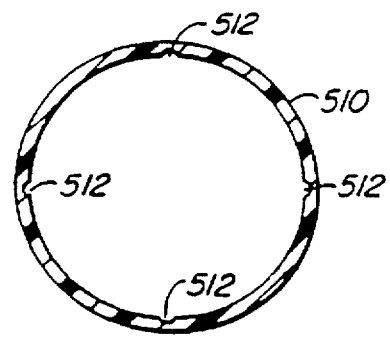
FIG. 5 is a cross-sectional view of an alternative housing embodiment constructed in accordance with the principles of the present invention.

Grooves may additionally or optionally be provided axially along the interior surface of the housing. For example, FIG. 5 shows a cross-sectional view of an exemplary housing 510 having four equally spaced grooves 512 along the interior surface of housing 510. The same or similar designs having housings provided with interior grooves are also suitable for side-on catheters. The grooves or channels will usually be oriented in a generally axial direction but it will also be possible to dispose the grooves helically so long as they provide or allow for proximal translation of the abraded material passed the head.

Referring now to FIGS. 6A–D some exemplary front-end abrasive heads in accordance with the principles of the present invention are presented. Both side views and end-on views are presented. Other abrasive heads consistent with the principles of the present invention will be apparent to those skilled in the art.

Figures 6A, 6B:
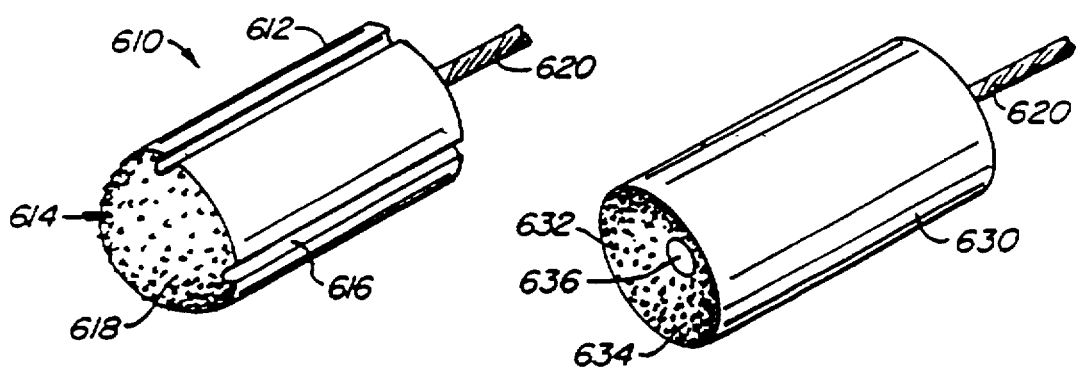
FIGS. 6A–D present perspective and end-on views of exemplary front-end abrasive heads constructed according to the principles of the present invention.

FIG. 6A shows head 610 having a cylindrical body 612 capped at its distal end by a rounded, e.g., hemispherical, abrasive surface 614. cylindrical body 612 is provided with four periodic grooves 616 which permit withdrawing abraded material from a region distal the head to a region proximal the head. An end-on view of the head shows the abrasive surface 618 periodically grooved around its periphery. Drive means 620 is attached to the proximal end of head 610 and extends proximally to a point external the patient's body.

8

FIG. 6B shows an alternative head design in which head 630 has a cylindrical body and a concave depression 632 provided at its distal end. An end-on view of head 630 shows an abrasive surface 634 having a circular periphery and an orifice 636 provided central to the surface through which a guidewire (not shown) may pass. Preferably, when a guidewire is employed, the wire will pass through the interior of head 630 via orifice 636 and will extend through an axial lumen provided interior drive means 620. The concave design of this and other such heads is expected to further assist in containing particles released upon grinding.

Figure 6C:
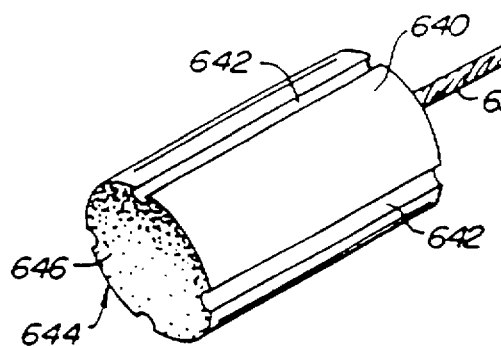

FIG. 6C shows another embodiment of an abrasive rotatable member of the present invention. Rotatable member 640 has a cylindrical body in which periodic grooves 642 are axially provided. The distal end 644 of rotatable member 640 has a recessed abrasive surface 646. The periphery of abrasive surface 646 is grooved at points corresponding to periodic grooves 642.

Figure 6D:
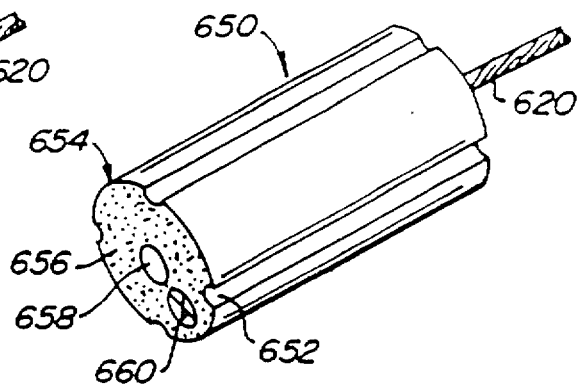

FIG. 6D presents a further embodiment of an abrasive rotatable member according to the principles of the present invention. Rotatable head 650 has a substantially cylindrical body provided with periodic grooves 652 running axially along its surface. The distal end 654 of head 650 has a substantially planar abrasive surface 656 attached thereto. The periphery of surface 656 has indentations accommodating periodic grooves 652. The center of surface 656 is provided with orifice 658 through which a guidewire may pass. Imaging transducer 660, e.g., an ultrasonic transducer, is affixed to surface 656.

2. Side-on Catheters

The abrasive heads of the present invention that are suitable for use in side-on catheters are comprised of the same or similar materials and are constructed analogously to the heads described above for front-end catheters. However, the side-on catheters of the present invention can be contrasted from front-end designs in that side-on designs allow use of a pull-type abrasive head, in which an abrasive surface is provided on the proximal end of the head.

Referring now to FIG. 2, housing 218 is provided with aperture 220. Preferably, aperture 220 is provided as an elongated slit in housing 218. Housing 218 further defines internal region 222 in which an abrasive head (not shown) will be provided. Moreover, internal region 224 will be at least partially occupied by target stenotic material and debris during operation of the device. Inflatable balloon 224 is provided opposite aperture 220 and external to housing 218. During inflation of inflatable balloon 224, an inflation medium is passed into balloon interior 228 provided between balloon 224 and housing 218. Likewise, deflation of balloon 224 occurs upon removal of inflation medium from the balloon interior 228. Inflation and deflation operations are described more fully below.

Referring now to FIGS. 7A–E, exemplary side-on abrasive heads are presented. Thus, in FIG. 7A, abrasive head 710 is comprised of a cylindrical region 712 and a conical region 714 distal to the cylindrical region. Conical region 714 is provided with an abrasive surface, which preferably extends over the entirety of the conical region. The cylindrical region 712 of head 710 is provided with periodic grooves 716 which allow passage of particles and fluid from distal head 710 to proximal head 710. Orifice 718 is provided in the distal tip of conical region 714 to allow passage of a guidewire. Drive means 720 is attached proximally to head 710 to allow translation and/or rotation of head 710 to contact the abrasive surface of the head against stenotic material.

Figure 7A:
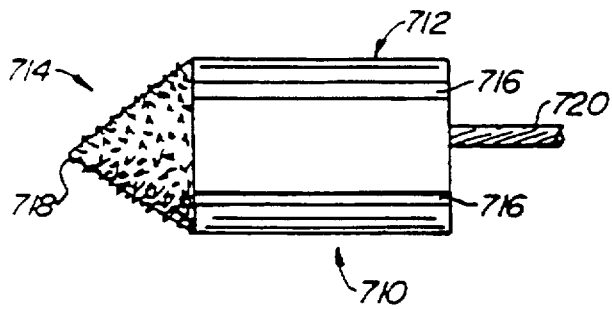
FIGS. 7A–E present perspective views of exemplary side-on abrasive heads constructed according to the principles of the present invention.
Figure 7B:
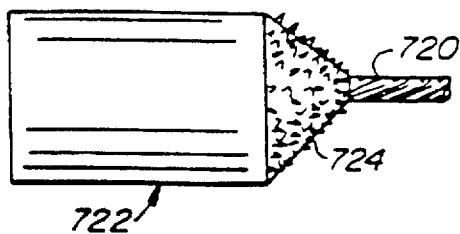

FIG. 7B depicts another preferred embodiment of an abrasive head suitable for removing stenotic material via a side-on atherectomy catheter. Thus, the head is comprised of cylindrical region 722 proximally attached to conical region 724. Conical region 724 has an abrasive surface, preferably extending over the entirety of region 724. The proximal-most tip of conical region 724 is attached to drive means 720.

Figure 7C:
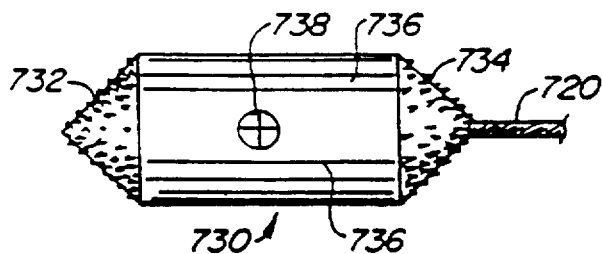

FIG. 7C presents a further preferred embodiment of a side-on abrasive head. Thus, the head comprises cylindrical region 730 attached at its distal and proximal ends to conical regions 732 and 734, respectively. Both regions 732 and 734 are provided with abrasive surfaces. Cylindrical region 730 is provided with periodic grooves 736 and is further provided with transducer 738. The proximal terminus of region 734 is attached to drive means 720.

Figure 7D:
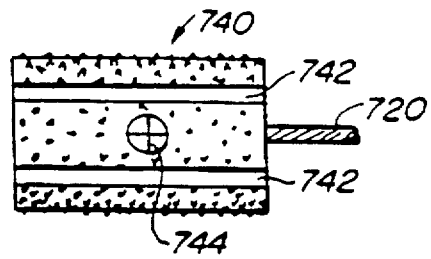

FIG. 7D shows a further preferred embodiment of a suitable side-on abrasive head in which an abrasive surface is provided over at least part of cylindrical region 740. Cylindrical region 740 is further provided with periodic grooves 742 as described above. Transducer 744 is provided in a recess on the surface of region 740.

Figure 7E:
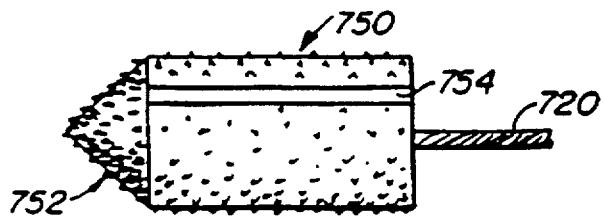

In FIG. 7E, the abrasive head is comprised of two conjoined abrasive regions. Thus, cylindrical region 750 is joined to conical region 752 provided distally to cylindrical region 750. Groove 754 is provided axially along cylindrical region 750.

Clearly, other designs of abrasive heads are contemplated in accordance with the principles of the present invention. Such designs will be readily apparent to one skilled in the art.

C. Means for Withdrawing Material

A means for withdrawing dislodged stenotic material from within the housing for the abrasive head is provided internal the catheter. Such provision permits removal of debris generated by the grinding process soon after it is produced, thereby greatly reducing the likelihood of emboli being released into the vascular system. Provision of such withdrawing means integrally to the catheter body also precludes the need for a means for withdrawing debris that is independent of the catheter.

Generally, the means for withdrawing abraded material will be the same for front-end or side-on catheters. However, some distinctions between front-end and side-on embodiments with respect to provision of the withdrawing means are envisioned and are described below.

Preferably, the means for withdrawing abraded stenotic material will principally employ an aspiration means in communication with the housing chamber internal the housing. Such means will ensure a negative pressure is maintained within the housing chamber relative to the surrounding vascular system, thereby minimizing the chance of emboli release from the housing chamber. The location selected for the aspiration opening within the housing is noncritical; however, it will preferably be distal the housing chamber and relatively near the aperture of the housing in order to minimize the time abraded material is retained within the housing.

Additionally, the means for withdrawing abraded material from the housing chamber may include a flushing means in communication with the chamber. The flushing means will employ a biocompatible flushing medium. Suitable flushing media are well-known to those skilled in the art and include saline and electrolyte solutions.

Care must be taken to ensure that the introduction of flushing media into the region internal the housing does not significantly promote release of emboli into the vascular system. Since release of emboli from within the housing will most likely occur through the aperture of the housing, flushing media will preferably be introduced into the housing chamber at a point within the housing that is as distant from the aperture as possible.

Further, it is preferred that the point selected within the housing for introducing the flushing medium will be chosen so as to maximize the coverage, or "sweep," of flushing media throughout the interior of the housing. Such provision will favor separation of the introduction point of the flushing medium from the point selected for the aspiration opening.

An exemplary preferred embodiment of the above-described means for withdrawing abraded material is presented in FIG. 9. Thus, the distal region 910 of a side-on catheter has flexible tube 912 attached to housing 914. Housing 914 is provided with an aperture 916 and with inflatable balloon 918 located opposite the aperture. Abrasive head 920 is located in housing chamber 922 internal housing 914 and is connected at its proximal end to drive means 924. Drive means 924 extends proximally through a lumen provided in flexible tube 912. A moveable guidewire will pass through a lumen provided internal in drive means 924. The guidewire will extend through the entire length of catheter 910 and will extend proximally and distally therefrom, as described more fully herein below.

An inflation medium will be introduced into catheter 910 via inflation lumen 926 provided in flexible tube 912. The inflation medium will pass through orifice 928 provided at the proximal extremity of housing 914 and into inflation region 930 located between balloon 918 and housing 914.

Flexible tube 912 is further provided with aspiration lumen 932 which extends axially therethrough and terminates distally in aspiration orifice 934 located at the interface between housing chamber 922 and flexible tube 912. Flexible tube 912 is further provided axially with flushing lumen 936 which extends distally to the proximal end of flushing tube 938 provided within housing chamber 922. Flushing tube 938 and flushing lumen 936 are met so as to prevent leakage of flushing medium there between. Flushing medium will pass through a lumen provided in flushing tube 938 until reaching flushing orifice 940 located distally in housing chamber 922.

Other embodiments incorporating the means for withdrawing abraded material from within the housing will be apparent to the skilled practitioner in view of the principles of the present invention.

D. Imaging Transducers

Frequently, an imaging means will be employed to afford a transluminal image of a diseased region of the patient's vascular system. Preferably, an ultrasonic transducer will be used to generate the imaging medium. A preferred transducer, its associated circuitry, and a preferred mode of operation are described in U.S. Pat. No. 4,794,931; incorporated herein by reference.

For example, FIG. 7D shows a cylindrical abrasive head suitable for use in a side-on catheter device according to the principles of the present invention. Transducer 744 is attached to the exterior of abrasive rotatable member 740. The transducer 744 will preferably be positioned in a recess provided in the surface of member 740. The recess will be sufficient to ensure that transducer 744 does not interfere with abrasion of atheromic material. Typically, transducer means 744 will be circular in shape and will have an outer diameter of 0.025–0.100 inches.

E. Guidewires

The catheters of the present invention will usually be used in conjunction with a guidewire. The guidewire will be either a fixed or moveable type. When a fixed guidewire is used, the distal end of the catheter will be secured to the guidewire. The guidewire will help to identify the vascular channel through which the catheter will pass, thereby assisting in placement of the distal end of the catheter adjacent stenotic material.

When a moveable guidewire is employed the guidewire will be first inserted into a patient's vascular system. The guidewire will pass to the target stenotic material. The distal end of the catheter will be guided to the site of occlusion by the guidewire. Usually, the guidewire will pass through an orifice provided in the distal tip of the catheter and will pass through the interior of the housing, typically via a lumen provided in the abrasive head. The guidewire will extend proximally through a lumen provided for such purpose in the catheter until the guidewire exits the patient's body.

FIGS. 8A–C present cross-sectional views of exemplary catheter bodies incorporating a lumen for passage of a guidewire therethrough. For example, FIG. 8A shows flexible tube 810 of the catheter body provided with lumen 812. Lumen 812 affords passage of drive means 814 which is itself provided with guidewire lumen 816. Flexible tube 810 is further provided with lumens 818, 820, and 822 which provide, respectively, means for aspirating dislodged material, means for flushing, and means for inflating an inflatable balloon.

A cross-sectional view of a catheter body having an alternative design, is shown in FIG. 8B. Thus, flexible tube 830 is provided with lumen 832 which accommodates drive means 834. As shown, drive means 834 need not have an axial lumen therethrough since the guidewire is passed through a separate lumen in flexible tube 830. Flexible tube 830 is further provided with lumens 836, 838, and 840 which allow, respectively, passage of a guidewire, aspirating means, and flushing means. Such a design is preferred when an inflatable balloon need not be present, e.g., when a front-end type catheter is employed.

FIG. 8C shows a cross-sectional view of another preferred embodiment, in which the guidewire passes through a lumen provided in the flexible tube of the catheter body. Thus, flexible tube 850 is provided with an axial lumen 852 which accepts drive means 854. Flexible tube 850 is further provided with lumens 856, 858, 860, and 862 which permit, respectively, passage of a guidewire, aspiration means, flushing means, and inflation means.

Other lumen patterns are consistent with the principles of the present invention and will be apparent to one skilled in the art. The inner diameter of a lumen provided for a guidewire will vary according to the diameter of the catheter but will typically be 0.0100.020 inches for smaller catheters and 0.025–0.040 inches for larger catheters.

F. Method of Use

Preferably, the distal end of the catheter and its abrasive head will be positioned adjacent target stenotic material with aid of X-ray fluoroscopy which readily identifies a catheter's location internal the patient. Such methods are well-known to those skilled in the art.

When a side-on catheter is employed, an inflation balloon is preferably located opposite the target deposit to cause the material to penetrate the aperture of the housing containing the abrasive head. The abrasive surface of the head will grind against the stenotic material through a combination of rotational and translational motion until the material is effectively removed from the vessel wall. Debris generated by the grinding process will be vacuum aspirated via an aspirating means external the patient. Preferably, a flushing medium is provided to assist withdrawal of the particles. The site of occlusion is inspected either concurrent with or subsequent to the grinding process to determine the extent of removal, preferably by means of an ultrasonic transducer located on the surface of the abrasive head. The above series of steps can be repeated at a different site of occlusion in the same manner.

Although the foregoing invention has been described in detail for purposes of clarity and understanding, it will be obvious that certain modifications may be practiced within the scope of the appended claims. For example, catheters constructed according to the principles of the present invention may be equipped with two balloon members to better anchor the catheter in the vascular system. Also, when two balloons are provided, they may be offset from directly opposite the aperture of the housing, thereby allowing removal of a portion of the housing directly opposite the aperture. Such a configuration will allow imaging of the vessel wall directly opposite target stenoses.

What is claimed is:

1. A method for removing stenotic material from a patient's vascular system comprising the steps of:
   introducing a catheter having a housing into the vascular system, said catheter having an abrasive member devoid of cutting edges and contained substantially within the housing during abrasion; and
   contacting the stenotic material with said abrasive member, whereby the stenotic material is abraded and collected into the housing.

2. A method according to claim 1, wherein the abraded stenotic material is withdrawn from the housing by aspiration.

3. A method according to claim 2, wherein the abraded stenotic material is withdrawn from the housing by a combination of flushing and aspiration.

4. A method according to claim 1, further comprising imaging the vascular system with an ultrasonic transducer, mounted on the abrasive member.

5. A method according to claim 4 wherein the transducer has a proximal end and a distal end, and wherein the abrasive member extends longitudinally from at least the proximal end of the transducer to at least the distal end of the transducer.

6. A method according to claim 1, wherein the housing has an aperture, and further comprising the step of inflating at least one inflatable balloon attached to the housing so that the stenotic material penetrates the aperture of the housing.

7. A method according to claim 1, wherein the abrasive member is operated by translation in combination with rotation.

8. A method according to claim 1 wherein the abrasive member is substantially cylindrical.

9. A method for removing stenotic material from a patient's vascular system comprising the steps of:
   introducing a catheter having a housing into the vascular system, said catheter having an abrasive member devoid of cutting edges and contained substantially within the catheter during abrasion;
   contacting the stenotic material with said abrasive member, whereby the stenotic material is abraded; and
   collecting abraded stenotic material by means of flushing and aspiration within the catheter.

10. A method according to claim 9, wherein the abraded stenotic material is withdrawn from the housing by aspiration.

11. A method according to claim 10, wherein the abraded stenotic material is withdrawn from the housing by a combination of flushing and aspiration.

12. A method according to claim 9, further comprising imaging the vascular system with an ultrasonic transducer, mounted on the abrasive member.

13. A method according to claim 12 wherein the transducer has a proximal end and a distal end, and wherein the abrasive member extends longitudinally from at least the proximal end of the transducer to at least the distal end of the transducer.

14. A method according to claim 9, wherein the housing has an aperture, and further comprising the step of inflating at least one inflatable balloon attached to the housing so that the stenotic material penetrates the aperture of the housing.

15. A method according to claim 9, wherein the abrasive member is operated by translation in combination with rotation.

16. A method according to claim 9 wherein the abrasive member is substantially cylindrical.

17. A method for removing stenotic material from a patient's vascular system comprising the steps of:
  introducing a catheter having a housing into the vascular system, said catheter having an abrasive member contained completely within the catheter during abrasion; and
  contacting the stenotic material with said abrasive member, whereby the stenotic material is abraded and collected by the catheter.

18. A method according to claim 17, wherein the abraded stenotic material is withdrawn from the housing by aspiration.

19. A method according to claim 18, wherein the abraded stenotic material is withdrawn from the housing by a combination of flushing and aspiration.

20. A method according to claim 17, further comprising imaging the vascular system with an ultrasonic transducer, mounted on the abrasive member.

21. A method according to claim 20 wherein the transducer has a proximal end and a distal end, and wherein the abrasive member extends longitudinally from at least the proximal end of the transducer to at least the distal end of the transducer.

22. A method according to claim 17, wherein the housing has an aperture, and further comprising the step of inflating at least one inflatable balloon attached to the housing so that the stenotic material penetrates the aperture of the housing.

23. A method according to claim 17, wherein the abrasive member is operated by translation in combination with rotation.

24. A method according to claim 17 wherein the abrasive member is substantially cylindrical.

25. A method for removing stenotic material from a patient's vascular system comprising the steps of:
  introducing a catheter having a housing, said catheter having an abrasive member contained completely within the housing during abrasion;
  contacting the stenotic material with said abrasive member, whereby the stenotic material is abraded; and
  collecting abraded stenotic material by means of flushing and aspiration within the catheter.

26. A method according to claim 25, wherein the abraded stenotic material is withdrawn from the housing by aspiration.

27. A method according to claim 26, wherein the abraded stenotic material is withdrawn from the housing by a combination of flushing and aspiration.

28. A method according to claim 25, further comprising imaging the vascular system with an ultrasonic transducer, mounted on the abrasive member.

29. A method according to claim 28 wherein the transducer has a proximal end and a distal end, and wherein the abrasive member extends longitudinally from at least the proximal end of the transducer to at least the distal end of the transducer.

30. A method according to claim 25, wherein the housing has an aperture, and further comprising the step of inflating at least one inflatable balloon attached to the housing so that the stenotic material penetrates the aperture of the housing.

31. A method according to claim 25, wherein the abrasive member is operated by translation in combination with rotation.

32. A method according to claim 25 wherein the abrasive member is substantially cylindrical.

33. A method for imaging and removing stenotic material in a patient's vascular system comprising the steps of:
  introducing a catheter into the vascular system, said catheter having an abrasive member with an ultrasound transducer mounted thereon, said abrasive member remaining substantially within the catheter during abrasion;
  contacting the stenotic material with said abrasive member, causing the stenotic material to be abraded; and
  imaging the vascular system with the ultrasound transducer.

34. A method according to claim 33 wherein the imaging is performed substantially concurrently with the contacting.

35. A method according to claim 33 wherein the abraded material is withdrawn from the catheter by aspiration.

36. A method according to claim 33, wherein the catheter has a housing with an aperture, and further comprising the step of inflating a balloon attached to the housing so that the stenotic material enters the aperture.

37. A method according to claim 33, wherein the abrasive member is operated by translation and rotation.

38. A method according to claim 37, wherein the abrasive member is substantially cylindrical.

39. A method according to claim 33 wherein the abrasive member is substantially cylindrical.

40. A method according to claim 33 wherein the transducer has a proximal end and a distal end, and wherein the abrasive member extends longitudinally from at least the proximal end of the transducer to at least the distal end of the transducer.

41. A method for removing stenotic material from a patient's vascular system comprising the steps of:
  introducing a catheter having a housing into the vascular system, said catheter having an elongate cylindrical abrasive member contained substantially within the housing during abrasion; and
  contacting the stenotic material with said abrasive member, whereby the stenotic material is abraded and collected into the housing.

42. A method according to claim 41, further comprising the step of withdrawing abraded stenotic material from the housing by aspiration.

43. A method according to claim 42, wherein the abraded stenotic material is withdrawn from the housing by a combination of flushing and aspiration.

44. A method according to claim 41, further comprising the step of imaging the vascular system with an ultrasonic transducer that is mounted on the abrasive member.

45. A method according to claim 44 wherein the transducer has a proximal end and a distal end, and wherein the abrasive member extends longitudinally from at least the proximal end of the transducer to at least the distal end of the transducer.

46. A method according to claim 44, wherein the abrasive member is devoid of cutting edges.

47. A method according to claim 46 wherein the transducer has a proximal end and a distal end, and wherein the abrasive member extends longitudinally from at least the proximal end of the transducer to at least the distal end of the transducer.

48. A method according to claim 46, wherein the abrasive member is completely within the housing during abrasion.

49. A method according to claim 48 wherein the transducer has a proximal end and a distal end, and wherein the abrasive member extends longitudinally from at least the proximal end of the transducer to at least the distal end of the transducer.

50. A method according to claim 44, wherein the abrasive member is completely within the housing during abrasion.

51. A method according to claim 50 wherein the transducer has a proximal end and a distal end, and wherein the abrasive member extends longitudinally from at least the proximal end of the transducer to at least the distal end of the transducer.

52. A method according to claim 41, further comprising the step of inflating a balloon attached to the housing to cause the stenotic material to penetrate an aperture of the housing.

53. A method according to claim 41, wherein the abrasive member is operated by translation in combination with rotation.

54. A method according to claim 41, wherein the abrasive member is devoid of cutting edges.

55. A method according to claim 54, wherein the abrasive member is contained completely within the housing during abrasion.

56. A method according to claim 41, wherein the abrasive member is contained completely within the housing during abrasion.

* * * * *